(12) United States Patent
Tang

(10) Patent No.: US 7,507,834 B2
(45) Date of Patent: Mar. 24, 2009

(54) SUBSTITUTED ANILINOPYRAZOLES

(75) Inventor: Jun Tang, Tsukuba (JP)

(73) Assignee: SmithKline Beechan Corporation, Philadelphia, PA (US)

( * ) Notice: Subject to any disclaimer, the term of this patent is extended or adjusted under 35 U.S.C. 154(b) by 539 days.

(21) Appl. No.: 10/547,013

(22) PCT Filed: Feb. 25, 2004

(86) PCT No.: PCT/US2004/005615

§ 371 (c)(1),
(2), (4) Date: Aug. 25, 2005

(87) PCT Pub. No.: WO2004/076414

PCT Pub. Date: Sep. 10, 2004

(65) Prior Publication Data

US 2006/0142284 A1 Jun. 29, 2006

Related U.S. Application Data

(60) Provisional application No. 60/450,365, filed on Feb. 27, 2003.

(51) Int. Cl.
*C07D 231/38* (2006.01)
*C07D 413/10* (2006.01)
(52) U.S. Cl. .................... 548/371.7; 544/114
(58) Field of Classification Search .............. 548/371.7; 544/114

See application file for complete search history.

(56) References Cited

U.S. PATENT DOCUMENTS 4,803,216 A * 2/1989 Appleton et al. ............ 514/407

5,486,534 A 1/1996 Lee et al.

FOREIGN PATENT DOCUMENTS

WO 01/79198 10/2001
WO 02/18346 3/2002

OTHER PUBLICATIONS

Cancer and Metastasis Reviews (1998), 17(1), 91-106.*
Science (1999), vol. 286, 531-537.*
Cancer [online], [retrieved on Jul. 6, 2007]. Retrieved from the Internet, URL; http://www.nlm.nih.gov/medlineplus/cancer.html>.*
Cancer [online], [retrieved on Jul. 6, 2007]. Retrieved from the Internet, URL; http://en.wikipedia.org/wiki/Cancer>.*
Medical Encyclopedia: Psoriasis [online], [retrieved on Apr. 2, 2008]. Retrieved from the Internet, URL; http://www.nlm.nih.gov/medlineplus/ency/article/000434>.*
Derivative (chemisty) [online], [retrieved on Apr. 2, 2008]. Retrieved from the Internet, URL; http://en.wikipedia.org/wiki/Derivative_%28chemistry%29>.*
Advanced Drug Delivery Reviews (2001) 48, 3-26.*
Tang, Jun et al., "Anilinopyrazole as selective CDK2 inhibitors: design, synthesis, biological evaluaion, and x-ray crystallographic analysis," *Bioorganic & Medicinal Chemistry Letters*, V13 N 18, 2003, pp. 2985-2988.

* cited by examiner

*Primary Examiner*—Rei-Tsang Shiao
*Assistant Examiner*—Shawquia Young
(74) *Attorney, Agent, or Firm*—John L. Lemanowicz; William T. Han; Kathryn L. Coulter

(57) ABSTRACT

The present invention relates to anilinopyrazole derivatives, methods for the preparation of such anilinopyrazoles, and use of such anilinopyrazoles in the treatment of certain diseases or conditions. In particular, the present invention relates to a nilinopyrazole derivatives useful as CDK2 inhibitors and use of the anilinopyrazoles in the treatment of disorders mediated by inappropriate CDK2 activity.

17 Claims, No Drawings

SUBSTITUTED ANILINOPYRAZOLES

CROSS-REFERENCE TO RELATED APPLICATIONS

This application is filed pursuant to 35 U.S.C. § 371 as a United States National Phase Application of International Application No. PCT/US2004/005615, filed Feb. 27, 2004, which claims the benefit of U.S. Provisional Application No. 60/450,365, filed Feb. 27, 2003, now abandoned.

FIELD OF THE INVENTION

The present invention relates to anilinopyrazole derivatives, methods for the preparation of such anilinopyrazoles, and use of such anilinopyrazoles in the treatment of certain diseases or conditions. In particular, the present invention relates to anilinopyrazole derivatives useful as CDK2 inhibitors and use of the anilinopyrazoles in the treatment of disorders mediated by inappropriate CDK2 activity.

BACKGROUND OF THE INVENTION

Effective chemotherapy, as well as radiotherapy, for cancer treatment, which has acceptable toxicity to normal cells, is a continuing goal in the oncology field. Numerous cytotoxic agents are used in the treatment of cancer, including cytotoxic agents that adversely affect rapidly dividing cells, including normal cells, that are in the process of cell division. Typically, such agents may have effect on the cell cycle at G1—the period between mitosis and DNA synthesis; S—the period of DNA synthesis; G2—the pre-mitotic interval; and/or M—the period of mitosis and are termed phase specific agents. Such agents are not effective in Go, the quiescent or resting cell phase. Therefore, such anti-neoplastic agents are active against cells in the process of cell division and are most effective against cancers that have a large growth fraction, that is, tumors that have a high percentage of dividing cells.

Protein kinases catalyze the phosphorylation of various residues in proteins including proteins involved in the regulation of cell growth and differentiation. Protein kinases play a critical role in the control of cell growth and differentiation and are key mediators of cellular signals leading to the production of growth factors and cytokines. See, for example, Schlessinger and Ullrich, Neuron 1992, 9, 383. The signals mediated by protein kinases have also been shown to control growth, death and differentiation in the cell by regulating the processes of the cell cycle.

Progression through the eukaryotic cell cycle is controlled by a family of protein kinases called cyclin dependent kinases (CDKs) and their interaction with a family of proteins termed cyclins (Myerson, et al., EMBO Journal 1992, 11, 2909-17). The coordinate activation and inactivation of different cyclin/CDK complexes is necessary for normal progression through the cell cycle (Pines, Trends in Biochemical Sciences 1993, 18, 195-7; Sherr, Cell 1993, 73, 1059-1065.). Both the critical G1-S and G2-M transitions are controlled by the activation of different cyclin/CDK activities. In G1, both cyclin D/CDK4 and cyclin E/CDK2 are thought to mediate the onset of S-phase. Progression through S-phase requires the activity of cyclin A/CDK2 whereas the activation of cyclin A/cdc2 (CDK1) and cyclin B/cdc2 are required for the onset of metaphase. It is not surprising, therefore, that the loss of control of CDK regulation is a frequent event in hyperproliferative diseases and cancer. (Pines, Current Opinion in Cell Biology 1992, 4, 144-8; Lees, Current Opinion in Cell Biology 1995, 7, 773-80; Hunter and Pines, Cell 1994, 79,573-82).

The present invention relates to novel compounds which are effective in inhibiting CDK2. The inhibition of CDK2 should arrest cells in G1 phase and prevent them from entering cell cycle. Thus compounds of the invention have utility in the treatment or prevention of cancer and other hyperproliferative diseases such as psoriasis.

SUMMARY OF THE INVENTION

In a first aspect, the instant invention relates a compound of the formula I, or a salt, solvate, or a physiologically functional derivative thereof

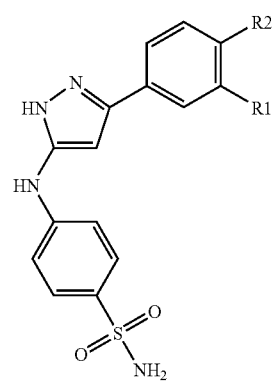

in which
R1 is hydrogen, halogen, —OMe, —OH, —NH$_2$, or —NHSO$_2$CH$_3$, or
R1 is a radical of the formula

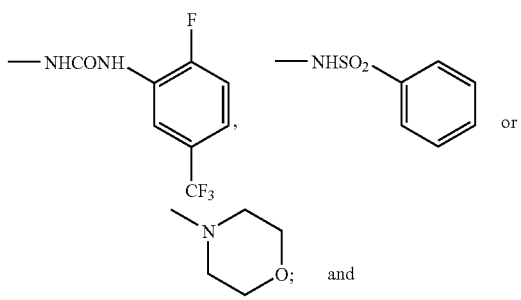

R2 is hydrogen, chlorine, —OMe, —OH, —NO$_2$, or —NH$_2$.

In a second aspect, the instant invention relates a method of inhibiting CDK2 protein in a mammal; comprising, administering to the mammal a therapeutically effective amount of a compound of the formula I, or a salt, solvate, or a physiologically functional derivative thereof.

In a third aspect of the present invention, there is provided a pharmaceutical composition including a therapeutically effective amount of a compound of formula I, or a salt, solvate, or a physiologically functional derivative thereof and one or more of pharmaceutically acceptable carriers, diluents and excipients.

In a fourth aspect of the present invention, there is provided the use of a compound of formula I, or a salt, solvate, or a physiologically functional derivative thereof in the preparation of a medicament for use in the treatment or prevention of a disease caused by inappropriate cell cycle resulting from the imbalance or inappropriate activity of CDK2 protein, including but not limited to, cancer and hyperproliferative diseases, such as psoriasis.

In a fifth aspect, the present invention relates to a method of treating or preventing a disease caused by inappropriate cell cycle from the imbalance or inappropriate activity of CDK2 protein including, but not limited to, cancer and other hyperproliferative diseases such as psoriasis; comprising administering to a mammal a therapeutically effective amount of a compound of formula I, or a salt, solvate, or a physiologically functional derivative thereof and one or more of pharmaceutically acceptable carriers, diluents and excipients.

In a six aspect, the present invention relates to a method of treating or preventing cancer and other hyperproliferative diseases, such as psoriasis; comprising administering to a mammal a therapeutically effective amount of a compound of formula I, or a salt, solvate, or a physiologically functional derivative thereof and one or more of pharmaceutically acceptable carriers, diluents and excipients.

In a seventh aspect, the present invention relates to chemical intermediates for making a compound of formula I.

In an eight aspect, the present invention relates to processes for making a compound of formula I.

DETAILED DESCRIPTION

The following terms may appear in the specification. If they appear, the following definitions will apply.

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein, the term "halogen" refers to fluorine (F), chlorine (Cl), bromine (Br), or iodine (I).

As used herein, the term "optionally" means that the subsequently described event(s) may or may not occur, and includes both event(s), which occur, and events that do not occur.

As used herein, the term "physiologically functional derivative" refers to any pharmaceutically acceptable derivative of a compound of the present invention, for example, an ester or an amide, which upon administration to a mammal is capable of providing (directly or indirectly) a compound of the present invention or an active metabolite thereof. Such derivatives are clear to those skilled in the art, without undue experimentation, and with reference to the teaching of Burger's Medicinal Chemistry And Drug Discovery, 5th Edition, Vol 1: Principles and Practice, which is incorporated herein by reference to the extent that it teaches physiologically functional derivatives.

As used herein, the term "solvate" refers to a complex of variable stoichiometry formed by a solute (in this invention, a compound of formula I or a salt or physiologically functional derivative thereof) and a solvent. Such solvents for the purpose of the invention may not interfere with the biological activity of the solute. Examples of suitable solvents include, but are not limited to, water, methanol, ethanol and acetic acid. Preferably the solvent used is a pharmaceutically acceptable solvent. Examples of suitable pharmaceutically acceptable solvents include, without limitation, water, ethanol and acetic acid. Most preferably the solvent used is water.

As used herein, the term "substituted" refers to substitution with the named substituent or substituents, multiple degrees of substitution being allowed unless otherwise stated.

Certain of the compounds described herein may contain one or more chiral atoms, or may otherwise be capable of existing as two enantiomers. Accordingly, the compounds of this invention include mixtures of enantiomers as well as purified enantiomers or enantiomerically enriched mixtures. Also included within the scope of the invention are the individual isomers of the compounds represented by formula I above as well as any wholly or partially equilibrated mixtures thereof. The present invention also covers the individual isomers of the compounds represented by the formulas above as mixtures with isomers thereof in which one or more chiral centers are inverted. Also, it is understood that all tautomers and mixtures of tautomers are included within the scope of the compounds of formula I.

Typically, the salts of the present invention are pharmaceutically acceptable salts. Salts encompassed within the term "pharmaceutically acceptable salts" refer to non-toxic salts of the compounds of this invention. Salts of the compounds of the present invention may comprise acid addition salts derived from a nitrogen on a substituent in the compound of formula I. Representative salts include the following salts: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylbromide, methylnitrate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, tannate, tartrate, teoclate, tosylate, triethiodide, trimethylammonium and valerate. Other salts, which are not pharmaceutically acceptable, may be useful in the preparation of compounds of this invention and these form a further aspect of the invention.

While it is possible that, for use in therapy, therapeutically effective amounts of a compound of formula I, as well as salts, solvates and physiological functional derivatives thereof, may be administered as the raw chemical, it is possible to present the active ingredient as a pharmaceutical composition. Accordingly, the invention further provides pharmaceutical compositions, which include therapeutically effective amounts of compounds of the formula I and salts, solvates and physiological functional derivatives thereof, and one or more pharmaceutically acceptable carriers, diluents, or excipients. The compounds of the formula I and salts, solvates and physiological functional derivatives thereof, are as described above. The carrier(s), diluent(s) or excipient(s) must be acceptable in the sense of being compatible with the other ingredients of the formulation and not deleterious to the recipient thereof. In accordance with another aspect of the invention there is also provided a process for the preparation of a pharmaceutical formulation including admixing a compound of the formula I, or salts, solvates and physiological functional derivatives thereof, with one or more pharmaceutically acceptable carriers, diluents or excipients.

Pharmaceutical formulations may be presented in unit dose forms containing a predetermined amount of active ingredient per unit dose. Such a unit may contain, for example, 0.5 mg to 1 g, preferably 1 mg to 700 mg, more preferably 5 mg to 100 mg of a compound of the formula I, depending on the condition being treated, the route of administration and the age, weight and condition of the patient, or pharmaceutical formulations may be presented in unit dose forms containing a predetermined amount of active ingredient per unit dose. Preferred unit dosage formulations are those containing a daily dose or sub-dose, as herein above recited, or an appropriate fraction thereof, of an active ingredient. Furthermore, such pharmaceutical formulations may be prepared by any of the methods well known in the pharmacy art.

Pharmaceutical formulations may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax or the like.

The compounds of formula I, and salts, solvates and physiological functional derivatives thereof, can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of formula I, and salts, solvates and physiological functional derivatives thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles and mouth washes.

Pharmaceutical formulations adapted for rectal administration may be presented as suppositories or as enemas.

Pharmaceutical formulations adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists, which may be generated by means of various types of metered, dose pressurised aerosols, nebulizers or insufflators.

Pharmaceutical formulations adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the formulations may include other agents conventional in the art having regard to the type of formulation in question, for example those suitable for oral administration may include flavouring agents.

A therapeutically effective amount of a compound of the present invention will depend upon a number of factors including, for example, the age and weight of the animal, the precise condition requiring treatment and its severity, the nature of the formulation, and the route of administration, and will ultimately be at the discretion of the attendant physician or veterinarian. However, an effective amount of a compound of formula I for the treatment or prevention of a condition caused by inappropriate cell cycle resulting from the imbalance or inappropriate activity of CDK2 protein, including but not limited to, cancer and hyperproliferative diseases, such as psoriasis, will generally be in the range of 0.1 to 100 mg/kg body weight of recipient (mammal) per day and more usually in the range of 1 to 10 mg/kg body weight per day. Thus, for a 70 kg adult mammal, the actual amount per day would usually be from 70 to 700 mg and this amount may be given in a single dose per day or more usually in a number (such as two, three, four, five or six) of sub-doses per day such that the total daily dose is the same. An effective amount of a salt or solvate, or physiologically functional derivative thereof, may be determined as a proportion of the effective amount of the compound of formula I per se. It is envisaged that similar dosages would be appropriate for treatment of the other conditions.

Method of Preparation

Compounds of general formula I may be prepared by methods known in the art of organic synthesis as set forth in part by the following synthetic schemes, or variants thereof. In all of the schemes described below, it is well understood that protecting groups for sensitive or reactive groups are employed where necessary in accordance with general principles of chemistry. Protecting groups are manipulated according to standard methods of organic synthesis (T. W. Green and P. G. M. Wuts (1991) Protecting Groups in Organic Synthesis, John Wiley & Sons). These groups are removed at a convenient stage of the compound synthesis using methods that are readily apparent to those skilled in the art. The selection of processes as well as the reaction conditions and order of their execution shall be consistent with the preparation of compounds of formula I. Those skilled in the art will recognize if a stereocenter exists in compounds of formula I. Accordingly, the present invention includes both possible stereoisomers and includes not only racemic compounds but the individual enantiomers as well. When a compound is desired as a single enantiomer, it may be obtained by stereospecific synthesis or by resolution of the final product or any convenient intermediate. Resolution of the final product, an intermediate, or a starting material may be effected by any suitable method known in the art. See, for example, Stereochemistry of Organic Compounds by E. L. Eliel, S. H. Wilen, and L. N. Mander (Wiley-Interscience, 1994).

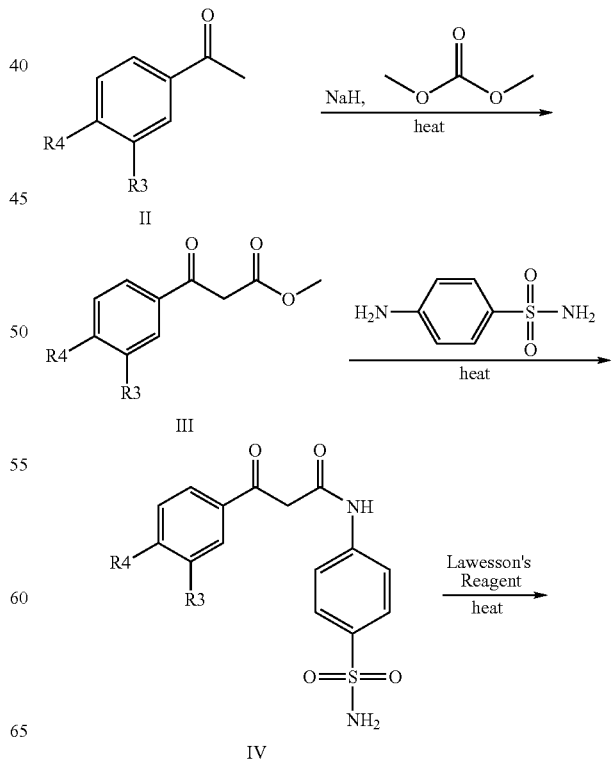

-continued

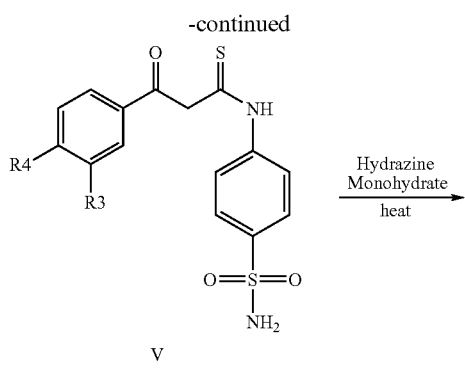

V

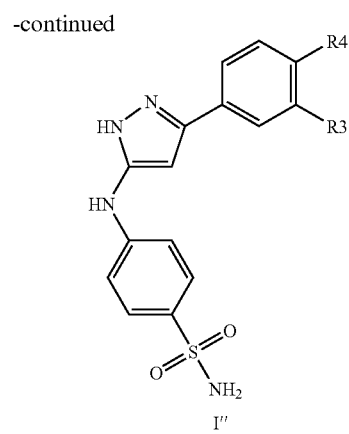

I″

Scheme C

[Scheme showing compound VIII (acetophenone with R3, R4) + H2N-sulfonyl-phenyl-NCS, heat]

[Compound IX: ketone-thioamide intermediate with sulfonamide, Hydrazine Monohydrate, heat]

IX

[Compound I‴: pyrazole with NH-phenyl-sulfonamide and R3/R4-phenyl]

I‴

Scheme B

[Compound VI: dithiol structure with R3, R4] + H2N-C6H4-SO2NH2, heat

[Compound VII: thiol-enamine intermediate], Hydrazine Monohydrate, heat

VII

Briefly in Scheme A, a compound of formula II is reacted with dimethyl carbonate with a suitable base, such as sodium hydride, to afford a compound of formula III. A compound of formula III is subsequently reacted with sulfanylamide to afford a compound of formula IV. A compound of formula IV is reacted with Lawesson's Reagent to afford thioamide of formula V which is subsequently reacted with hydrazine to afford a compound of formula I′.

In Scheme B, a compound of formula VI is reacted with sulfanylamide to afford a compound of formula VII. A compound of formula VII is reacted with hydrazine to yield a compound of formula I".

In Scheme C, a compound of formula VIII is reacted with sulfamoylphenylisocyanate with a base, such as LiN(TMS)$_2$, to afford a compound of formula IX. A compound of formula IX is reacted with hydrazine to afford a compound of formula I'".

In Schemes A-B, R3 and R4 are R1 and R2, respectively, which are as previously defined, or they are groups which can be converted to R1 and R2, respectively. Conversion of R3 and R4 into respective R1 and R2 are exemplified in the actual Examples below.

SPECIFIC EMBODIMENTS—EXAMPLES

As used herein the symbols and conventions used in these processes, schemes and examples are consistent with those used in the contemporary scientific literature, for example, the Journal of the American Chemical Society or the Journal of Biological Chemistry. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

g (grams);
L (liters);
μL (microliters);
mg (milligrams);
mL (milliliters);
psi (pounds per square inch);
M (molar);
i.v. (intravenous);
MHz (megahertz);
mmol (millimoles);
min (minutes);
mp (melting point);
mM (millimolar);
Hz (Hertz);
mol (moles);
rt (room temperature);
h (hours);
Tr (retention time);
MeOH (methanol);
TEA (triethylamine);
TFAA (trifluoroacetic anhydride);
DMSO (dimethylsulfoxide);
DME (1,2-dimethoxyethane);
DCE (dichloroethane);
DMPU (N,N'-dimethylpropyleneurea);
IBCF (isobutyl chloroformate);
HOSu (N-hydxoxysuccinimide);
mCPBA (meta-chloroperbenzoic acid;
BOC (tert-butyloxycarbonyl);
DCC (dicyclohexylcarbodiimide);
Ac (acetyl);
TMSE (2-(trimethylsilyl)ethyl);
TIPS (triisopropylsilyl);
DMAP (4-dimethylaminopyridine);
ATP (adenosine triphosphate);
DMEM (Dulbecco's modified Eagle medium);
TLC (thin layer chromatography);
RP (reverse phase);
i-PrOH (isopropanol);
TFA (trifluoroacetic acid);
THF (tetrahydrofuran);
AcOEt (ethyl acetate);
DCM (dichloromethane);
DMF (N,N-dimethylformamide);
(CDI (1,1-carbonyldiimidazole);
HOAc (acetic acid);
HOBT (1-hydroxybenzotriazole);
EDC (ethylcarbodiimide hydrochloride);

-continued

FMOC (9-fluorenylmethoxycarbonyl);
CBZ (benzyloxycarbonyl);
atm (atmosphere);
TMS (trimethylsilyl);
TBS (t-butyldimethylsilyl);
BSA (bovine serum albumin)
HRP (horseradish peroxidase);
HPLC (high pressure liquid chromatography);
BOP (bis(2-oxo-3-oxazolidinyl)phosphinic chloride);
TBAF (tetra-n-butylammonium fluoride);
HBTU (O-Benzotriazole-1-yl-N,N,N',N'-tetramethyluronium hexafluorophosphate).
HEPES (4-(2-hydroxyethyl)-1-piperazine ethane sulfonic acid);
DPPA (diphenylphosphoryl azide);
fHNO3 (fumed HNO3); and
EDTA (ethylenediaminetetraacetic acid).

All references to ether are to diethyl ether; brine refers to a saturated aqueous solution of NaCl. Unless otherwise indicated, all temperatures are expressed in ° C. (degrees Centigrade). All reactions are conducted under an inert atmosphere at room temperature unless otherwise noted.

$^1$H NMR spectra were recorded on a Brucker AVANCE-400. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), quint (quintet), m (multiplet), br (broad).

LC-MS were recorded on a micromass ZMD and Waters 2690. All mass spectra were taken under electrospray ionization (ESI) methods. Most of the reactions were monitored by thin-layer chromatography on 0.25 mm E. Merck silica gel plates (60F-254), visualized with UV light, 5% ethanolic phosphomolybdic acid or p-anisaldehyde solution. Flash column chromatography was performed on silica gel (230-400 mesh, Merck).

Example 1

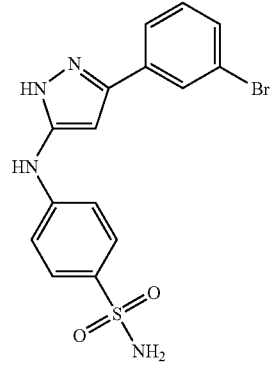

4-[5-(3-Bromo-phenyl)-2H-pyrazol-3-ylamino]-benzenesulfonamide (Ia)

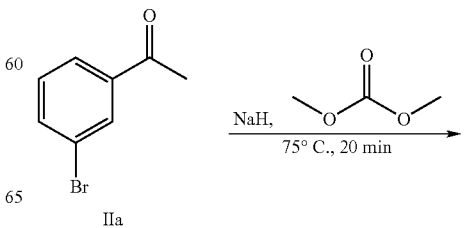

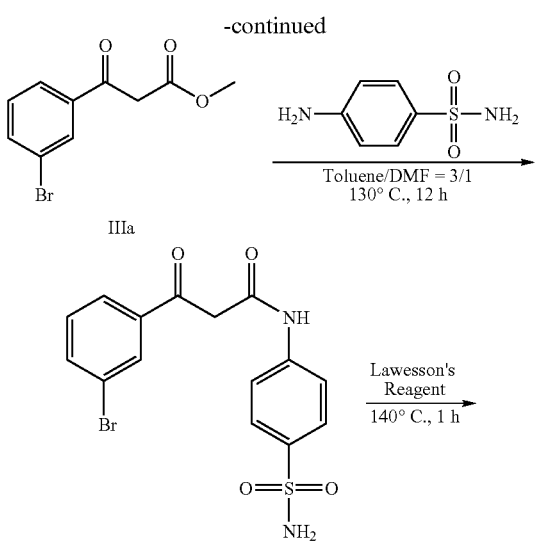

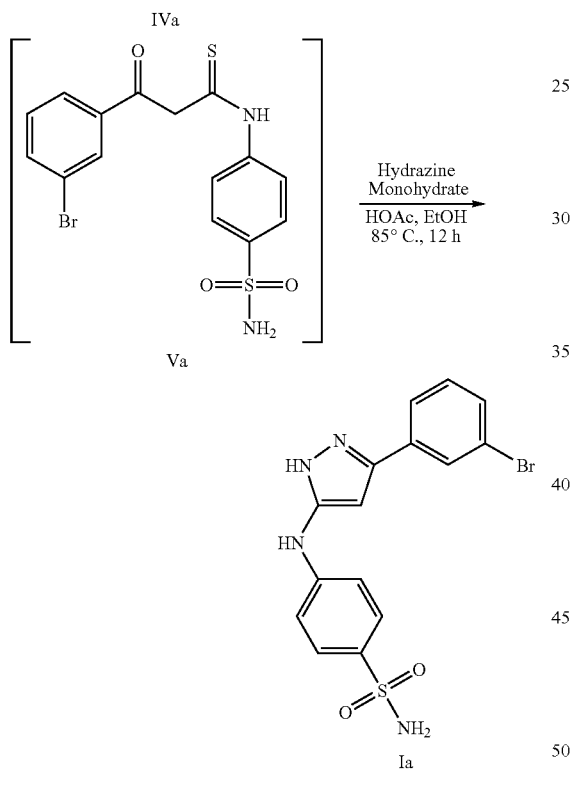

To a suspension of dimethyl carbonate (72 g) and 60% oily sodium hydride 6.4 g at 75° C. was added 3-bromoacetophenone Ia (80 mmol, 15.9 g) dropwise. The reaction was maintained at gentle state by adjusting the addition rate (exothemic). After the addition was complete, the reaction was heated at 75° C. for 20 min, then cooled to rt. A small amount of water was added to quench the excess base and then dimethyl carbonate was evaporated. After acidifying the residue with aqueous 10% HCl, it was extracted with ether (2×) and the combined ether layer were washed with water and dried. Purification by silica gel chromatography (AcOEt/Hexane=1/10) gave 17.48 g (85%) of compound IIIa.

A mixture of IIIa (10 mmol, 2.57 g) and sulfanylamide (11 mmol, 1.89 g) in toluene (30 ml) and DMF (10 ml) was heated at 130° C. for 12 h. After cooling to rt, the resulting precipitation was filtered and dried in vacuo to give 2.18 g (55%) of IVa.

A suspension of IVa (0.49 mmol, 194 mg) and Lawesson's reagent (0.51 mmol, 208 mg) in toluene (12 ml) was heated to 140° C. for 1 h, and then concentrated in vacuo. The residue was directly dissolved in ethanol (5 mL) without any purification. Hydrazine hydrate (0.25 mL) and HOAc (a few drops) were added, and the reaction was allowed to stir at 85° C. for 12 h before it was concentrated in vacuo. The residue was extracted with AcOEt, and AcOEt layer washed with brine, dried over Na$_2$SO$_4$. Purification by HPLC (Gilson) gave 14 mg (7.3%) of compound Ia. $^1$HNMR: (400 MHz, DMSO-d6) ppm 6.44 (s, 1H), 7.06 (s, 2H), 7.42 (m, 3H), 7.55 (d, 1H, J=7.6 Hz), 2H, J=8.8 Hz), 7.76 (d, 1H, J=7.6 Hz), 8.00 (t, 1H, J=1.8 Hz), 9.10 (s, 1H), 12.76 (s, 1H). LC/MS: m/z 393(M−1)$^−$, 395 (M+1)$^+$.

Example 2

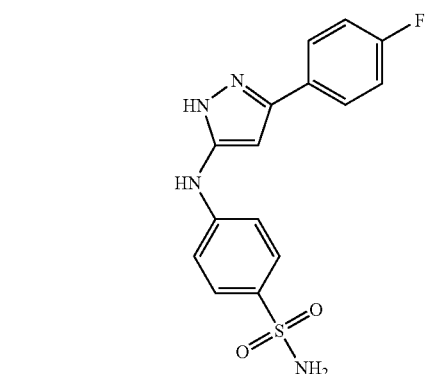

4-[5-(4-Fluoro-phenyl)-2H-pyrazol-3-ylamino]-benzenesulfonamide (Ib)

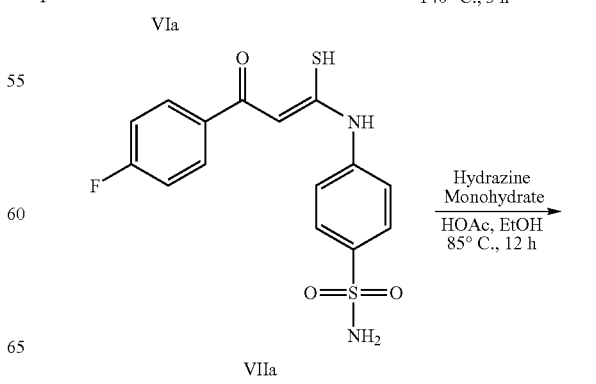

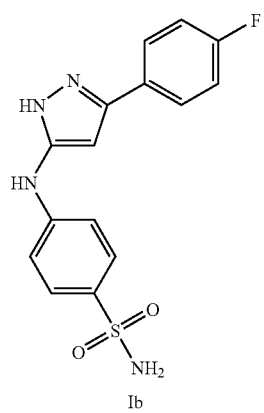

Ib

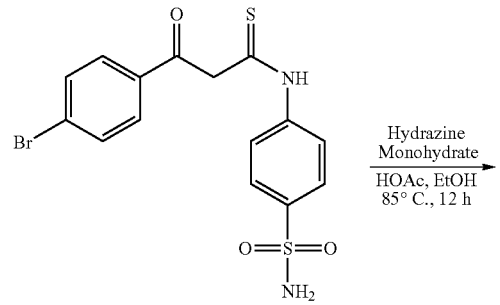

IXa

A mixture of VIa (3 mmol, 642.8 mg) and sulfanylamide (3 mmol, 516.6 mg) in toluene (20 ml) and DMF (2 ml) was heated at 140° C. for 3 h, and then concentrated in vacuo. The residue was directly dissolved in ethanol (20 mL) without any purification. Hydrazine hydrate (1 mL) and HOAc (a few drops) were added, and the reaction mixture was allowed to stir at 85° C. for 12 h before it was concentrated in vacuo. The residue was extracted with AcOEt, and AcOEt layer washed with brine, dried over $Na_2SO_4$. Partially evaporating the solvent gave precipitation. The solid was collected by filtration, then recrystallized from MeOH/AcOEt, and dried in vacuo to give 111 mg (0.33 mmol, 11.1%) of compound Ib. $^1$HNMR: (400 MHz, DMSO-d6) ppm 6.33 (s, 1H), 7.04 (brs, 2H), 7.31 (m, 2H), 7.43 (m, 2H), 7.63 (d, 2H, J=8.8 Hz), 7.79 (dd, 2H, J=3.3, 8.6 Hz), 9.04 (s, 1H), 12.64 (s, 1H). LC/MS: m/z 331(M−1)[−], 333 (M+1) [+].

Example 3

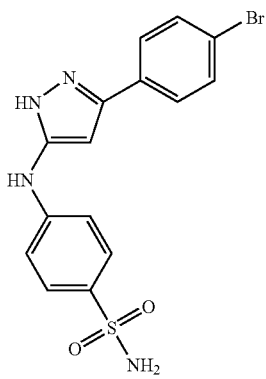

4-[5-(4-Bromo-phenyl)-2H-pyrazol-3-ylamino]-benzenesulfonamide (Ic)

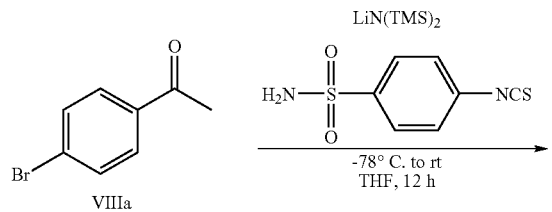

Lithium bis(trimethylsilyl)amide (2.2 mL, 1.0 M in THF, 2.2 mmol) was slowly added to a mixture of the corresponding acetophenone (1.0 mmol) and 4-sulfamoylphenylisocyanate (1.0 mmol, 214 mg) in dry THF (7.5 mL) at −78° C. under argon. The reaction was stirred for 30 min and then warmed to rt for another 12 h. It was quenched with MeOH and concentrated in vacuo. The resultant crude thioamide was directly dissolved in ethanol (10 mL) without any purification. Hydrazine hydrate (0.5 mL) and HOAc (a few drops) were added, and the reaction mixture was allowed to stir at 85° C. for 12 h before it was concentrated in vacuo. The residue was extracted with AcOEt, and AcOEt layer washed with brine, and dried over $Na_2SO_4$. Partially evaporating the solvent gave precipitation. The solid was collected by filtration and dried in vacuo to give 121 mg (0.307 mmol, 30.7%) of compound Ic as yellow solid. $^1$HNMR: (400 MHz, DMSO-d6) ppm 6.38 (s, 1H), 7.06 (brs, 2H), 7.43 (brs, 2H), 7.62 ~7.73 (m, 6H), 9.08 (s, 1H), 12.73 (s, 1H). LC/MS: m/z 391(M−1)[−], 393(M−1) [−], 393 (M+1)[+], 395(M+1)[+].

Example 4-6 compounds were made by the process as described in Example 3 (Scheme C).

Example 4

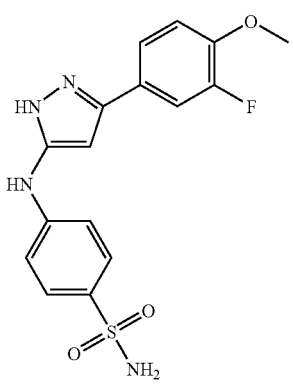

4-[5-(3-Fluoro-4-methoxy-phenyl)-2H-pyrazol-3-ylamino]-benzenesulfonamide (Id)

Compound Id was obtained in 10% yield with the procedure described in Example 3. $^1$HNMR: (400 MHz, DMSO-d6) ppm 3.88 (s, 3H), 6.32 (s, 1H), 7.05 (brs, 2H), 7.25 (t, 1H, J=8.8 Hz), 7.43 (m, 2H), 7.55 (d, 2H, J=8.3 Hz), 7.61~7.66 (m, 3H), 9.05 (s, 1H), 12.58 (s, 1H). LC/MS: m/z 361(M−1)$^-$, 363 (M+1)$^+$.

Example 5

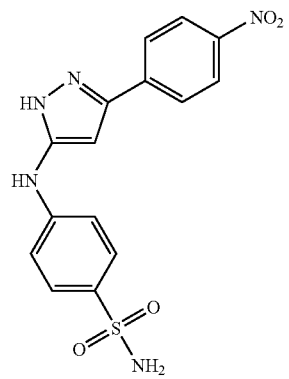

4-[5-(4-Nitro-phenyl)-2H-pyrazol-3-ylamino]-benzenesulfonamide (Ie)

Compound Ie was obtained in 19% yield with the procedure described in Example 3. $^1$HNMR: (400 MHz, DMSO-d6) ppm 6.61 (s, 1H), 7.08 (brs, 2H), 7.40 (m, 2H), 7.66 (d, 2H, J=8.8 Hz), 8.05 (d, 2H, J=8.8 Hz), 8.32 (d, 2H, J=8.8 Hz), 9.16 (s, 1H), 13.06 (s, 1H). LC/MS: m/z 358 (M−1)$^-$, 360 (M+1)$^+$.

Example 6

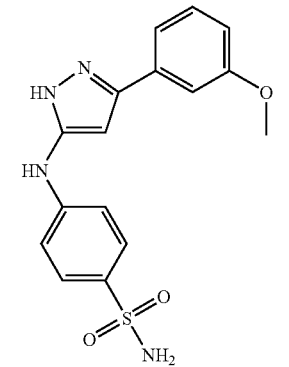

4-[5-(3-Methoxy-phenyl)-2H-pyrazol-3-ylamino]-benzenesulfonamide (If)

Compound If was obtained in 37.7% yield with the procedure described in Example 3. $^1$HNMR: (400 MHz, DMSO-d$_6$) ppm 3.82 (s, 3H), 6.36 (s, 1H), 6.92 (d, 1H, J=8.1 Hz), 7.05 (brs, 2H), 7.32~7.43 (m, 5H), 7.63 (d, 2H, J=8.8 Hz), 9.05 (s, 1H), 12.67 (s, 1 H). LC/MS: m/z 343 (M−1)$^-$, 345 (M+1)$^+$.

Example 7

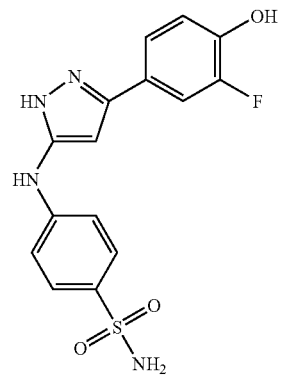

4-[5-(3-Fluoro-4-hydroxy-phenyl)-2H-pyrazol-3-ylamino]-benzenesulfonamide (Ig)

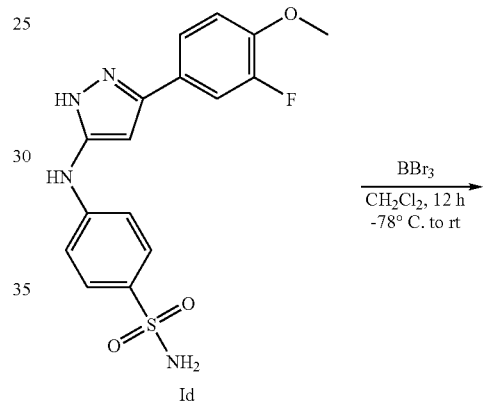

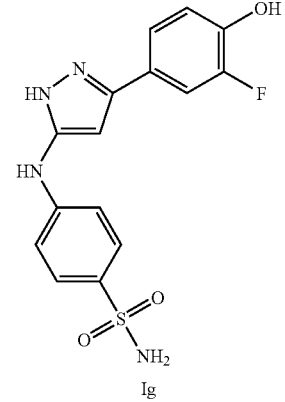

Compound Id (0.334 mmol, 121 mg) was stirred in dry CH$_2$Cl$_2$ (9 mL) at −78° C. Boron tribromide (1.67 mL, 1.0 M in CH$_2$Cl$_2$, 1.67 mmol) was slowly added, and the reaction stirred for 12 h while warming to rt. It was quenched with MeOH, concentrated in vacuo. The residue was dissolved into 1N NaOH aqueous and filtered to remove the undissolved precipitation. The filtrate was neutralized with aqueous 0.1 N HCl and extracted with AcOEt. Organics were washed with brine, dried over Na$_2$SO$_4$, and concentrated in vacuo to give 58 mg (50%) of compound Ig as a white solid.

$^1$HNMR: (400 MHz, DMSO-d$_6$) ppm 6.25 (s, 1H), 6.98~7.05 (m, 3H), 7.37~7.42 (m, 3H), 7.56 (dd, 1H, J=2.0, 12.3 Hz), 7.62 (d, 2H, J=8.8 Hz), 9.03 (s, 1H), 10.14 (s, 1H), 12.33(s, 1H). LC/MS: m/z 347 (M−1)⁻, 349 (M+1)⁺.

Example 8

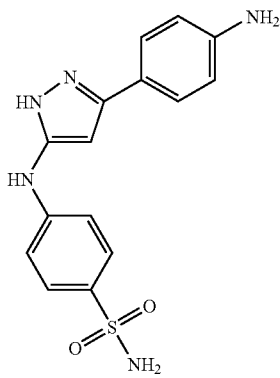

4-[5-(4-Amino-phenyl)-2H-pyrazol-3-ylamino]-benzenesulfonamide (Ih)

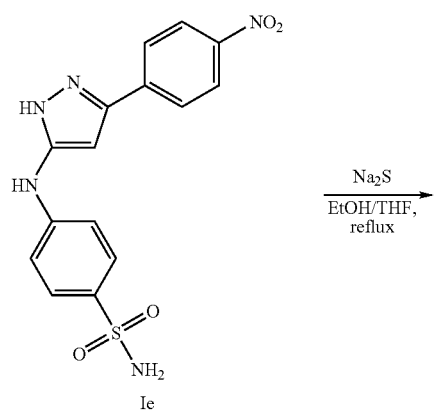

A mixture of compound Ie (0.57 mmol, 205 mg) and sodium sulfide nonahydrate (2.85 mmol, 684.5 mg) in EtOH (20 ml) and THF (10 ml) was heated to reflux for 5 h, and then concentrated in vacuo. The residue was extracted with AcOEt, washed with brine, dried over Na₂SO₄, and treated by BondElut SCX to give 173 mg (92%) of compound Ih. 1H NMR (400 MHz, DMSO-d6) ppm 5.34 (s, 2H), 6.05 (s, 1H), 6.59 (d, 2H, J=8.6 Hz), 7.03 (s, 2H), 7.38 (d, 2H, J=8.6 Hz), 7.43 (d, 2H, J=8.8 Hz), 7.61 (d, 2H, J=8.8 Hz), 8.96 (s, 1H), 12.23 (s, 1H). LC/MS: m/z 328 (M−1)⁻, 330 (M+1)⁺.

Example 9

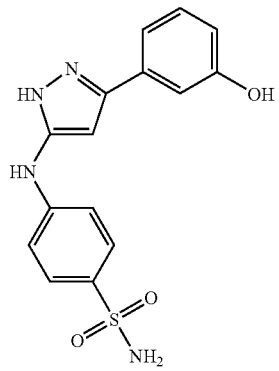

4-[5-(3-Hydroxy-phenyl)-2H-pyrazol-3-ylamino]-benzenesulfonamide (Ii)

Compound Ii was obtained in 42% yield with the similar procedure as described Example 7 from compound If. 1H NMR (400 MHz, DMSO-d6) ppm 6.24 (s, 1H), 6.76 (dd, 1H, J=1.8, 8.1 Hz), 7.05 (brs, 2H), 7.10~7.26 (m, 3H), 7.42 (d, 2H, J=8.6 Hz), 7.63 (d, 2H, J=8.8 Hz), 9.04 (s, 1H). LC/MS: m/z 329 (M−1)⁻, 331 (M+1)⁺.

Example 10

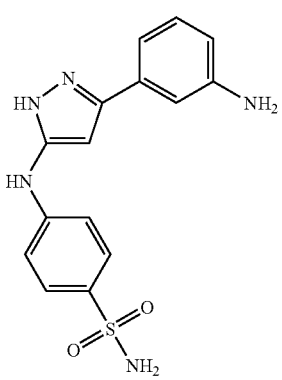

4-[5-(3-Amino-phenyl)-2H-pyrazol-3-ylamino]-benzenesulfonamide (Ij)

Compound Ij was obtained in 85% yield with the similar procedure as described in Example 8 from 4-[5-(3-nitro-phenyl)-2H-pyrazol-3-ylamino]-benzenesulfonamide, which was prepared with the similar procedure as described in Example 3. 1H NMR (400 MHz, DMSO-d6) ppm 5.19 (s, 2H), 6.12 (s, 1H), 6.55 (d, 1H, J =7.6 Hz), 6.86 (m, 2H), 7.05 (s, 2H), 7.08 (t, 1H, J=7.6 Hz), 7.44 (d, 2H, J=8.8 Hz), 7.63 (d, 2H, J=8.8 Hz), 9.02 (s, 1H), 12.48 (s, 1H). LC/MS: m/z 328 (M−1) ⁻, 330 (M+1)⁺. cl Example 11

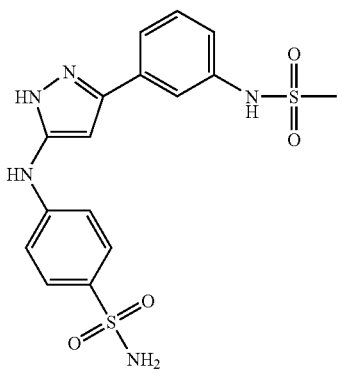

4-[5-(3-Methanesulfonylamino-phenyl)-2H-pyrazol-3-ylamino]-benzenesulfonamide (Ik)

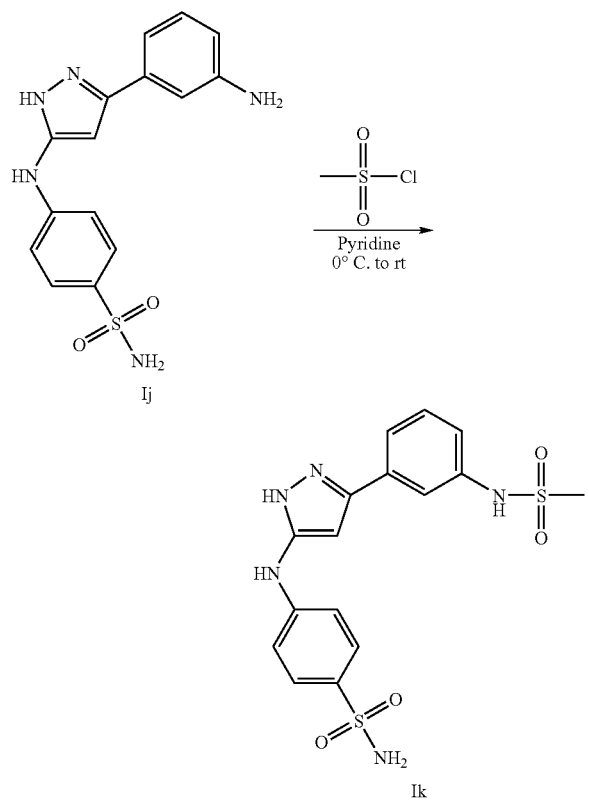

Methylsulfonylchloride (9.2 uL, 1.05 equiv.) was added to a solution of compound Ij (0.1 mmol, 33 mg) in pyridine (1 mL) at 0° C. The reaction was warmed to rt and stirred for another 4 h before it was concentrated in vacuo. A small amount of AcOEt, MeOH and CH$_2$Cl$_2$ were added to the residue and the resultant was sonicated to give precipitation. The solid was collected by filtration and dried in vacuo to give 21 mg (0.052 mmol, 51.5%) of compound Ik. 1H NMR (400 MHz, DMSO-d6) ppm 3.06 (s, 3H), 6.23 (s, 1H), 7.06 (s, 2H), 7.18 (d, 1H, J=7.1 Hz), 7.40~7.50 (m, 5H), 7.64 (d, 2H, J=8.8 Hz), 9.07 (s, 1H), 9.88 (s, 1H), 12.72 (s, 1H). LC/MS: m/z 406 (M−1)$^-$, 408 (M+1)$^+$.

Example 12-13 compounds were made by a similar process as described in Example 11.

Example 12

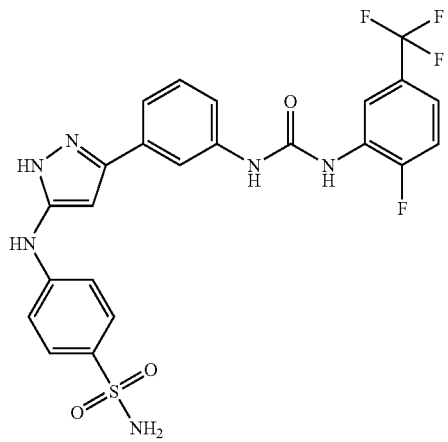

4-(5-{3-[3-(2-Fluoro-5-trifluoromethyl-phenyl)-ureido]-phenyl}-2H-pyrazol-3-ylamino)-benzenesulfonamide (Il)

Compound Il was obtained in 24.3% yield from compound Ij and 1-fluoro-2-isocyanato-4-trifluoromethyl-benzene. 1H NMR (400 MHz, DMSO-d6) ppm 6.27 (s, 1H), 7.06 (s, 2H), 7.39~7.54 (m, 7H), 7.64 (d, 2H, J=8.8 Hz), 7.79 (s, 1H), 8.64 (d, 1H, J=7.3 Hz), 9.00 (s, 1H), 9.07 (s, 1H), 9.29 (s, 1H), 12.69 (s, 1H). LC/MS: m/z 533 (M−1)$^-$, 535 (M+1)$^+$.

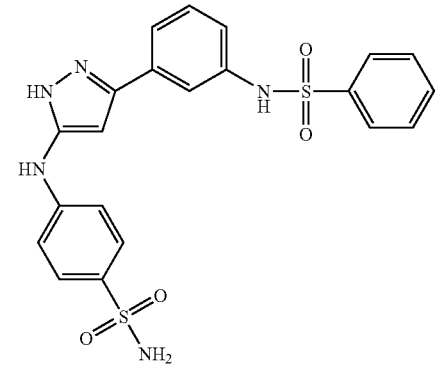

4-[5-(3-Benzenesulfonylamino-phenyl)-2H-pyrazol-3-ylamino]-benzenesulfonamide (Im)

Compound Im was obtained in 44.7% yield from compound Ij and benzenesulfonyl chloride. $^1$H NMR (400 MHz, DMSO-d$_6$) ppm 6.15 (s, 1H), 7.03 (d, 1H, J=7.8 Hz), 7.04 (brs, 2H), 7.30 (t, 1H, J=7.8 Hz), 7.39~7.43 (m, 4H), 7.54~7.65 (m, 5H), 7.80 (d, 2H, J=8.6 Hz), 9.06 (s, 1H), 10.45 (s, 1H). LC/MS: m/z 468 (M−1)$^-$, 470 (M+1)$^+$.

Example 14

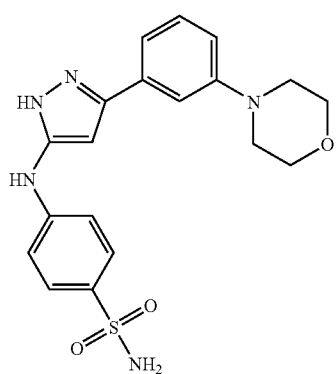

4-[5-(3-Morpholin-4-yl-phenyl)-2H-pyrazol-3-ylamino]-benzenesulfonamide (In)

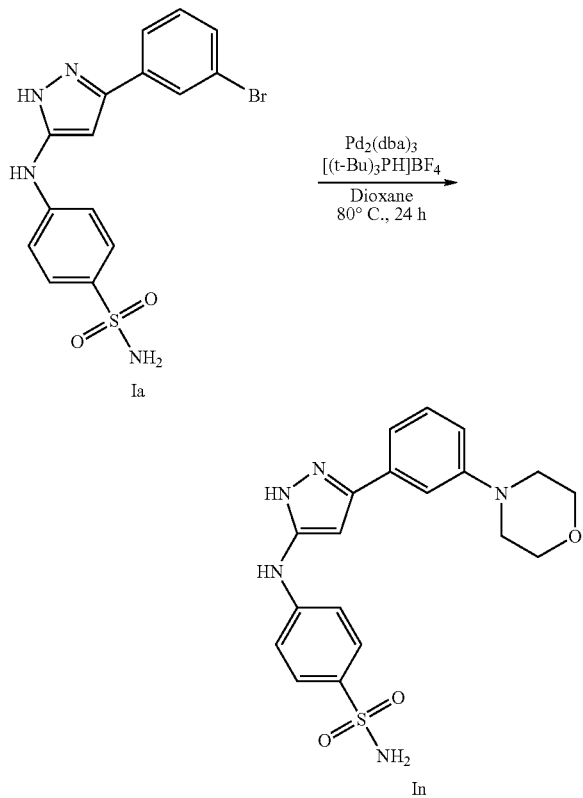

Compound Ia (0.13 mmol, 51 mg), t-BuONa (1.69 mmol, 162 mg), Pd$_2$(dba)$_3$ (0.026 mmol, 23.8 mg), and [(t-BU)$_3$PH]BF$_4$ (0.01 mmol, 30 mg) were added dry dioxane (1 mL) under argon followed by morpholine (1.3 mmol, 113 uL) and the reaction was stirred at 80° C. for 24 h. After cooling to rt, the reaction was extracted with AcOEt, and treated with BondElut SCX column. Evaporating the solvent gave a residue and the product was purified by BondElut NH2 (9% MeOH in AcOEt), which afforded compound In (17 mg, 42.5%). $^1$H NMR (400 MHz, DMSO-d6) ppm 3.18 (m, 4H), 3.76 (m, 4H), 6.35 (s, 1H), 6.93 (dd, 1H, J=1.8, 8.4 Hz), 7.05 (brs, 2H), 7.17 (d, 1H, J=7.6 Hz), 7.27~7.31 (m, 2H), 7.41 (d, 2H, J=7.3 Hz), 7.63 (d, 2H, J=8.8 Hz), 9.03 (s, 1H), 12.61 (s, 1H). LC/MS: m/z 398 (M−1)$^−$, 400 (M+1)$^+$.

The compounds of the present invention have valuable pharmacologic properties. Different compounds from this class are particularly effective at inhibiting CDK2. Representative data is shown in Table 1 following. Substrate phosphorylation assays were carried out as follows:

Cyclin dependent protein kinase 2 assays utilized the peptide Biotin-aminohexyl-ARRPMSPKKKA-NH2 (SEQ ID NO:1) as phosphoryl group acceptor. CDK2 was expressed utilizing a baculovirus expression system and was partially purified to comprise 20-80% of total protein, with no detectable competing reactions present. Typically, assays were performed by incubating enzyme (0.2-10 nM), with and without inhibitor, peptide substrate (1-10 nM), [g-32P]ATP (1-20 nM), and 10-20 mM Mg2+ for periods of time generally within the range 10-120 minutes. Reactions were terminated with 0.2-2 volumes of either 20% acetic acid or 50-100 mM EDTA buffered to pH 7 (substrate consumption <20%). The buffer employed in enzyme assay was 100 mM HEPES pH 7.5 containing 0.1 mg/mL BSA and 5% DMSO. Inhibitors were diluted in 100% DMSO prior to addition into the assay. Detection of peptide phosphorylation was accomplished by scintillation counting following either collection of peptide onto phosphocellulose filters (for reactions stopped with acetic acid), collection of peptide in wells of 96 well plates coated with Streptavidin (Pierce) (reactions were stopped with EDTA), or addition of Avidin coated Scintillant impregnated beads (Scintillation Proximity Assays from Amersham, reactions were stopped with EDTA). Counts detected by any of these methodologies minus the appropriate background (assays with additional 40 mM EDTA or lacking peptide substrate) were assumed to be proportional to the reaction initial rates, and IC50s were determined by a least squares fit to the equation CPM=Vmax*(1−([I]/(K+[I])))+nsb, or −pIC50s were determined by a fit to the equation CPM=nsb+(Vmax−nsb)/(1+(x/10x−pIC50)), where nsb are the background counts filters and washed four times with 75 mM phosphoric acid. Radioactivity was determined by liquid scintillation counting.

TABLE 1

| Compound no. | pIC$_{50}$ values |
|---|---|
| Ih | ++++ |
| Ij | +++ |
| Il | ++ |
| In | + |

| Legend | |
|---|---|
| pIC$_{50}$ values | Symbol |
| 9.99-9.0 | ++++ |
| 8.99-8.0 | +++ |
| 7.99-7.0 | ++ |
| 6.99-4.7 | + | pIC$_{50}$ = −log$_{10}$(IC$_{50}$)

What is claimed:

1. A compound of the formula I, or a salt, thereof

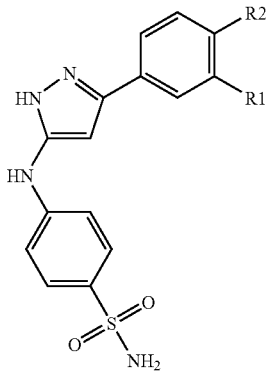

in which
R1 is hydrogen, halogen, —OMe, —OH, —NH$_2$, or —NHSO$_2$CH$_3$, or
R1 is a radical of the formula

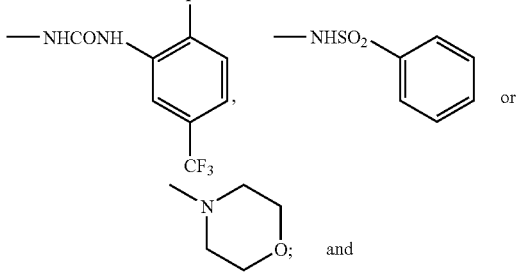

R2 is hydrogen, chlorine, —OMe, —OH, —NO$_2$, or —NH$_2$.

2. A pharmaceutical composition comprising a therapeutically effective amount of a compound of claim 1 and one or more of pharmaceutically acceptable carriers, diluents and excipients.

3. A compound of claim 1 in which the halogen is bromo or fluoro.

4. A compound of claim 1 that is 4-[5-(3-bromo-phenyl)-2H-pyrazol-3-ylamino]-benzenesulfonamide.

5. A compound of claim 1 that is 4-[5-(4-fluoro-phenyl)-2H-pyrazol-3-ylamino]-benzenesulfonamide.

6. A compound of claim 1 that is 4-[5-(4-bromo-phenyl)-2H-pyrazol-3-ylamino]-benzenesulfonamide.

7. A compound of claim 1 that is 4-[5-(3-fluoro-4-methoxy-phenyl)-2H-pyrazol-3-ylamino]-benzenesulfonamide.

8. A compound of claim 1 that is 4-[5-(4-nitro-phenyl)-2H-pyrazol-3-ylamino]-benzenesulfonamide.

9. A compound of claim 1 that is 4-[5-(3-methoxy-phenyl)-2H-pyrazol-3-ylamino]-benzenesulfonamide.

10. A compound of claim 1 that is 4-[5-(3-fluoro-4-hydroxy-phenyl)-2H-pyrazol-3-ylamino]-benzenesulfonamide.

11. A compound of claim 1 that is 4-[5-(4-amino-phenyl)-2H-pyrazol-3-ylamino]-benzenesulfonamide.

12. A compound of claim 1 that is 4-[5-(3-hydroxy-phenyl)-2H-pyrazol-3-ylamino]-benzenesulfonamide.

13. A compound of claim 1 that is 4-[5-(3-amino-phenyl)-2H-pyrazol-3-ylamino]-benzenesulfonamide.

14. A compound of claim 1 that is 4-[5-(3-methanesulfonylamino-phenyl)-2H-pyrazol-3-ylamino]-benzenesulfonamide.

15. A compound of claim 1 that is 4-(5-{3-[3-(2-fluoro-5-trifluoromethyl-phenyl)-ureido]-phenyl}-2H-pyrazol-3-ylamino)-benzenesulfonamide.

16. A compound of claim 1 that is 4-[5-(3-benzenesulfonylamino-phenyl)-2H-pyrazol-3-ylamino]-benzenesulfonamide.

17. A compound of claim 1 that is 4-[5-(3-morpholin-4-yl-phenyl)-2H-pyrazol-3-ylamino]-benzenesulfonamide.

* * * * *